(12) United States Patent
Ruterjans et al.

(10) Patent No.: US 6,524,834 B1
(45) Date of Patent: Feb. 25, 2003

(54) DIISOPROPYL FLUOROPHOSPHATASE AND THE UTILIZATION AND PRODUCTION THEREOF

(75) Inventors: Heinz Ruterjans, Bad Homburg (DE); Stefan Dierl, Liederbach (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/622,820

(22) PCT Filed: Nov. 27, 2000

(86) PCT No.: PCT/EP99/01159

§ 371 (c)(1), (2), (4) Date: Feb. 23, 1999

(87) PCT Pub. No.: WO99/43791

PCT Pub. Date: Sep. 2, 1999

(30) Foreign Application Priority Data

Feb. 27, 1998 (DE) .......................... 198 08 192

(51) Int. Cl.[7] ........................ C12N 9/16; C12N 1/20; C07H 21/04
(52) U.S. Cl. .................. 435/196; 435/195; 435/252.3; 435/252.33; 435/254.11; 435/320.1; 435/262.5; 536/23.2; 536/23.5; 424/94.6
(58) Field of Search ............................ 435/195, 196, 435/252.3, 252.33, 254.11, 262.5, 267, 320.1; 424/94.6; 536/23.2, 23.5

(56) References Cited

U.S. PATENT DOCUMENTS

| | | | |
|---|---|---|---|
| 4,666,696 A | 5/1987 | Shultz | 423/659 |
| 5,550,311 A | 8/1996 | Young | 588/19 |
| 5,648,591 A | 7/1997 | Donecker et al. | 588/205 |

OTHER PUBLICATIONS

Untersuchungen an einem Phosphorsäureester spaltenden Enzym aus "Loligo vulgaris," (Lünzer Dissertation), 1992, Frankfurt, Germany (with English translated Summary attached), 141 pages.

Dierl, Ph.D. Thesis from Dr. Stefan Dierl, German, 159 pages.

Deschamps et al., *Comparative Biochemistry and Physiology*, 3, "Comparison of Organophosphorous Acid Anhydrolases from Different Species using Monoclonal Antibodies", pp. 765–768 (1993).

Aldridge, *Biochem. J. 53*, "Serum Esterases", pp. 117–124, (Feb. 1952).

Deschamps et al., Internet web page, titled "National Library of Medicine: IGM Full Record Screen", available at http://130.14.32.42/cgi–bin/VERSION A/IGM, with Abstract for Comp. Biochem. Physiol C, 106(3), pp. 765–768, (1993).

Dierl, English Abstract of the Ph.D. Thesis from Dr. Stefan Dierl, 2 pgs., (1995).

Hoskin et al., *Science, 215*, "Hydrolysis of Nerve Gas by Squid–Type Diisopropyl Phosphorofluoridate Hydrolyzing Enzyme on Agarose Resein", pp. 1255–1257, (Mar. 1982).

Hoskin et al., *Proc. Jerusalem Symp. Quantum Chem. Biochem., 7*, "Squid Nerve Type DFPase: A Consideration of Molecular Structures", pp. 209–211, (1974).

Hoskin et al., *Proc. Natl. Acad. Sci. USA, 55*, "Re–Examination of the Effect of DFP on Electrical and Cholinesterase Activity of Squid Giant Axon", pp. 1231–1235, (Mar. 1966).

Kopec–Smyth, Jr., et al., *Chem.–Biol. Interactions, 87*, "A Partial Primary Structure of Squid Hepatopancreas Organophosphorus Acid Anhydrolase", 49–54, (1993).

McGuinn et al., *Fundamental and Applied Toxicology, 21*, "The Encapsulation of Squid Diisopropylphosphorofluoridate–Hydrolyzing Enzyme within Mouse Erythrocytes", pp. 38–43, (1993).

Steinmann, *Dissertation Abstracts International, 51(5)*, "Characterization of multiple forms of Squid Organophosphorus Acid Anhydrase", p. 2161 B, (1990).

Wang, et al., *J Biochem. Toxicology*, vol. 8, No. 3, "Purification and Properties of a Diisopropy–Fluorophosphates from Squid Todarodes", pp. 161–166, (1993).

*Primary Examiner*—Nashaat T. Nashed
(74) *Attorney, Agent, or Firm*—Foley & Lardner

(57) ABSTRACT

The present application relates to a diisopropyl-fluorophosphatase from *Loligo vulgaris,* and to the amino acid and nucleic acid sequences encoding the enzyme. Also provided are vectors which contain the DNA sequence according to the invention, and to cells transformed with the base sequence according to the invention. Finally, the present application also provides a method for the production of the diisopropyl-fluorophosphatase and various types of use and areas of employment of the diisopropyl-fluorophosphatase, in particular the decontamination of contaminated habitats, the production of medicinal products for treating or detoxifying humans and animals, the impregnation of clothing and the use in analyses.

31 Claims, No Drawings

DIISOPROPYL FLUOROPHOSPHATASE AND THE UTILIZATION AND PRODUCTION THEREOF

The present invention relatesto a diisopropyl-fluorophosphatase (enzyme classification EC 3.1.8.2., called DFPase hereinafter) from *Loligo vulgaris,* to the base sequence encoding the enzyme, and to the use of the enzyme and a method for its production in transformed cells.

The term DFPase has a wide scope in the description of a class of enzymes able to hydrolyse diisopropyl fluorophosphate (DFP) and other organophosphorus compounds with a similar structure. The group of these organophosphorus compounds can be traced back to compounds of the following basic structure:

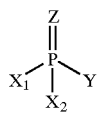

In this, Z represents oxygen or sulphur, Y represents a group which may, as H—Y compound, have acidic properties. These are, inter alia, anhydride groups (deprotonated acid groups)(in particular an F or CN group) or ester groups such as a thioester, an enol ester or a p-nitrophenyl ester group. The groups $X_1$ and $X_2$ may be straight- or branched-chain or cyclic alkoxy, alkyl, aryl, alkylamino or dialkylamino groups containing 1 to 15 carbon atoms. A large number of such compounds are or were used as insecticides. Other compounds are covered by the term of so-called nerve gases. The nerve gases of this class of compounds include, inter alia, DFP, tabun, soman, sarin, thylsarin and cyclosarin.

Reducing the stocks of these highly toxic compounds in the world is an increasing problem. In addition, it is necessary to find environmentally acceptable methods for decontaminating already contaminated areas of the environment.

The most important method to date for destroying large amounts of these substances comprises incineration at high temperatures.

In addition, for example, U.S. Pat. No. 4,666,696 deals with the destruction of nerve gases and other cholinesterase inhibitors by reduction with molten aluminium.

Further approaches to solving this problem comprise, for example, the use of physical methods. Thus, for example, U.S. Pat. No. 5,550,311 describes the thermal decomposition of toxic compounds (nerve gases) in an aqueous stream. Another approach is described in U.S. Pat. No. 5,648,591, in which chemical weapons such as, for example, sarin are broken down by activation in mechanical mills. All these methods have severe disadvantages in relation to their economic efficiency and their limited range of applications. Thus, for example, it is necessary in all these methods to feed the appropriate toxic substances into particular apparatuses, which makes, for example, use in the field difficult if not impossible.

Biological disposal of chemical weapons stocks and decontamination by microorganisms or enzymes which can be produced in large quantities might provide a simplification or a more effective approach to solving these problems.

The present invention therefore contrasts with the decontamination methods described above and builds on investigations by Aldrige as long ago as 1953. Aldridge observed that various tissues from different organisms contain enzymes which hydrolyse paraoxon, a cholinesterase inhibitor. Later investigations in 1966 by Hoskin and co-workers showed that the squid *Loligo pealii* contains a DFP-cleaving enzyme. Numerous investigations in this area have followed to the present day, but it has not yet been possible to sequence or even isolate a recombinant protein. The enzyme investigated by Hoskin could not be accurately characterized in terms of its molecular weight. Whereas Hoskin assumed a molecular weight of 26,600 Da, other research groups, for example Kopec-Smyth et al. (1993), regarded it as probable that the 26.6 kDa protein is only a fragment of a very unstable 42 kDa protein. A short amino acid sequence of a peptide fragment of this DFPase was published in 1993 by Ward and Deschamps. The sequence section described therein is not found in the claimed amino acid sequence of the present invention, for which reason it must be assumed that the DFPase from *Loligo pealii* differs distinctly from the DFPase of the present invention.

Similar proteins have been identified in a wide variety of organisms apart from *Loligo pealii.* Thus, they have been found inter alia in thermophilic or halophilic bacteria, in *E. coli, Proteus vulgaris, Saccharomyces cerevisiae, Pseudomonas diminuta,* Flavobacterium and the eukaryotic unicellular organism *Tetrahymena thermophilia,* and in insects and invertebrates. Detection has also been possible in mammals such as mice, rats, rabbits, pigs and humans. Despite the efforts of a large number of research groups concerned with enzymes which resemble in their specificity the DFPase from *Loligo vulgaris* of the present invention, none of these groups has succeeded incompletely elucidating the amino acid sequence, and the nucleotide sequence underlying the latter, of an enzyme corresponding to the present invention, in transforming the corresponding nucleotide sequence using a vector into a host cell, and thus in making industrial production possible in excellent purity. Although Dierl (1995, thesis, Johann Wolfgang Goethe University, Frankfurt/Main) was able during his research work to elucidate a partial sequence of the DFPase from *Loligo vulgaris,* no details of the amino acid sequence or nucleotide sequence are to be found in this study. The partial information provided by Dierl is incomplete and reproducibility of the results presented therein is impossible simply because of the unavailability to the public of the cDNA gene bank on which the study is based but which is not accessible to the public.

One of the objects of the present invention is to provide the complete and functioning DFP-cleaving enzyme from *Loligo vulgaris* and the nucleotide sequence encoding the enzyme in order to make industrial production of a genetic engineering type possible. A further object was to provide a DFPase which can be isolated on an industrial scale without loss of stability by fractional ammonium sulphate precipitation and which has its activity optimum at a neutral pH of about 7.5 and room temperature (about 25° C.). It was intended thereby not least to achieve the object of environmentally friendly, energy-saving disposal of nerve gases and insecticides. A further object to be achieved was to provide a storage- and solvent-stable DFPase. Thus, it was intended, for example, that a concentrated solution be stable with negligible loss of activity at 4° C. for a lengthy period. It was also intended that various solvents or solvent-containing aqueous media (for example 10% strength aqueous ethanolic solution) have no effect on the activity of the enzyme. A further object to be achieved was to provide a DFPase which is active in a wide variety of buffer systems. The provision of the DFPase was further intended to make it possible to decontaminate, detoxify and moreover detect acetylcholinesterase inhibitors which serve as substrate of the DFPase. The provision of such an enzyme is intended not only to make the industrial destruction of appropriate nerve gases or insecticides possible but also to provide the possibility of decontaminating contaminated habitats (soils, watercourses, etc.). A cloning in plants is also possible thereby. It is further conceivable to employ enzyme for producing medicinal products for detoxifying or treating humans and animals. This might involve the enzyme being employed, for example, locally in the form of a skin cream, parenterally in the form of a solution for infusion or inhalation, or else orally.

The said objects have been achieved by providing a DFPase of the following amino acid sequence (SEQ ID NO: 1):

```
Met Glu Ile Pro Val Ile Glu Pro Leu Phe Thr Lys Val Thr Glu Asp
1               5                   10                  15
Ile Pro Gly Ala Glu Gly Pro Val Phe Asp Lys Asn Gly Asp Phe Tyr
                20                  25                  30
Ile Val Ala Pro Glu Val Glu Val Asn Gly Lys Pro Ala Gly Glu Ile
                35                  40                  45
Leu Arg Ile Asp Leu Lys Thr Gly Lys Lys Thr Val Ile Cys Lys Pro
        50                  55                  60
Glu Val Asn Gly Tyr Gly Gly Ile Pro Ala Gly Cys Gln Cys Asp Arg
65                      70                  75                  80
Asp Ala Asn Gln Leu Phe Val Ala Asp Met Arg Leu Gly Leu Leu Val
                    85                  90                  95
Val Gln Thr Asp Gly Thr Phe Glu Glu Ile Ala Lys Lys Asp Ser Glu
                100                 105                 110
Gly Arg Arg Met Gln Gly Cys Asn Asp Cys Ala Phe Asp Tyr Glu Gly
            115                 120                 125
Asn Leu Trp Ile Thr Ala Pro Ala Gly Glu Val Ala Pro Ala Asp Tyr
        130                 135                 140
Thr Arg Ser Met Gln Glu Lys Phe Gly Ser Ile Tyr Cys Phe Thr Thr
145                 150                 155                 160
Asp Gly Gln Met Ile Gln Val Asp Thr Ala Phe Gln Phe Pro Asn Gly
                165                 170                 175
Ile Ala Val Arg His Met Asn Asp Gly Arg Pro Tyr Gln Leu Ile Val
                180                 185                 190
Ala Glu Thr Pro Thr Lys Lys Leu Trp Ser Tyr Asp Ile Lys Gly Pro
            195                 200                 205
Ala Lys Ile Glu Asn Lys Lys Val Trp Gly His Ile Pro Gly Thr His
        210                 215                 220
Glu Gly Gly Ala Asp Gly Met Asp Phe Asp Glu Asp Asn Asn Leu Leu
225                 230                 235                 240
Val Ala Asn Trp Gly Ser Ser His Ile Glu Val Phe Gly Pro Asp Gly
                245                 250                 255
Gly Gln Pro Lys Met Arg Ile Arg Cys Pro Phe Glu Lys Pro Ser Asn
                260                 265                 270
Leu His Phe Lys Pro Gln Thr Lys Thr Ile Phe Val Thr Glu His Glu
            275                 280                 285
Asn Asn Ala Val Trp Lys Phe Glu Trp Gln Arg Asn Gly Lys Lys Gln
        290                 295                 300
Tyr Cys Glu Thr Leu Lys Phe Gly Ile Phe
305                 310
```

The claimed diisopropyl-fluorophosphatase also embraces in this connection amino acid sequences which can be derived from the above sequence by a deletion, insertion and/or substitution of one or more amino acids, as long as the DFPase activity is retained. This also includes, of course, a truncation of the amino-and/or carboxy-terminal side.

This amino acid sequence according to the invention has as its basis a DNA sequence according to the invention which comprises a DNA sequence which codes for the DFPase from *Loligo vulgaris* and which comprises in a preferred embodiment the following nucleotide sequence (SEQ ID NO: 2).

The present invention further relates to a cell which is transformed with a DNA sequence according to the invention or a vector according to the invention. This cell can be, for example, a prokaryotic cell, preferably a Gram-negative prokaryotic cell, particular preferably a eubacterial cell. In one embodiment, this cell is an *E. coli* cell. The transfor-

```
ATGGAAATTC CAGTTATCGA ACCTCTTTTC ACAAAAGTGA CCGAAGATAT ACCAGGTGCA    60

GAGGGTCCCG TTTTTGACAA AAATGGCGAT TTTTATATCG TGGCCCCCGA AGTTGAAGTT   120

AACGGAAAAC CGGCGGGAGA AATTCTACGA ATCGATTTGA AAACAGGAAA GAAAACTGTG   180

ATCTGCAAAC CAGAAGTTAA TGGTTATGGA GGAATTCCTG CTGGCTGCCA ATGTGATCGA   240

GATGCCAACC AGCTGTTTGT GGCCGACATG AGACTCGGCT TGTTGGTCGT GCAAACTGAT   300

GGGACCTTTG AAGAGATTGC CAAAAAAGAC TCTGAAGGTA GAAGAATGCA GGGATGCAAT   360

GATTGCGCAT TTGATTATGA AGGTAACTTG TGGATCACTG CACCAGCTGG GGAAGTCGCA   420

CCTGCAGACT ACACCCGTTC AATGCAGGAA AAATTTGGCA GTATTTACTG CTTCACAACA   480

GATGGTCAAA TGATTCAAGT GGATACTGCT TTCCAGTTTC CAAATGGTAT TGCTGTTCGT   540

CACATGAACG ATGGCCGTCC TTACCAACTA ATTGTGGCTG AAACTCCAAC CAAGAAACTC   600

TGGAGTTATG ATATCAAAGG TCCAGCAAAG ATTGAAAACA AGAAAGTGTG GGGTCACATC   660

CCAGGTACTC ATGAAGGTGG TGCTGATGGA ATGGATTTTG ATGAAGACAA TAACCTTTTG   720

GTAGCCAACT GGGGGAGCTC ACACATCGAA GTGTTCGGCC CAGATGGGGG ACAGCCTAAA   780

ATGAGAATCC GTTGCCCATT TGAAAAACCC AGCAACTTGC ATTTCAAGCC CCAGACCAAA   840

ACCATTTTTG TCACGGAACA CGAGAACAAT GCTGTCTGGA AGTTTGAATG GCAAAGAAAT   900

GGCAAAAAAC AGTATTGTGA GACGTTAAAA TTTGGAATAT TT                     942
```

It is possible by modifications of the nucleotide sequence to adapt, for example, the substrate specificity, solubility and/or stability of the enzyme to the problems arising.

A further object of the present invention is to provide a vector which contains at least one copy of a DNA sequence according to the invention. This vector may be any prokaryotic or eukaryotic vector on which the DNA sequence according to the invention is present, preferably under the control of an expression signal. Expression signals include, inter alia, promoters, operators and enhancers. Promoters may be, for example, a T7 promoter or lac, tac, lacUV5 or $P_L$ promoters. Suitable prokaryotic vectors are, for example, chromosomal vectors such as, for example bacteriophages, (for example, bacteriophage λ) and extrachromosomal vectors such as, for example, plasmids, with circular plasmid vectors being preferred in this connection. The vector according to the invention may, on the other hand, also be a eukaryotic vector, for example a yeast vector or a vector suitable for higher cells, such as, for example, a plasmid vector or a viral vector. Vectors of the indicated types are familiar to the person skilled in the area of molecular biology so that no further details on this are necessary here. It is possible in a preferred embodiment to use as such vectors so-called secretion vectors which make it possible to express a protein which is a fusion between DFPase and a signal peptide, where the signal peptide is responsible for passing the protein through the cell membrane and being separated accurately from the DFPase by signal peptidases on secretion. Suitable signal peptides are, for example, a pelB, α or PHO1 signal peptide. The linkage of the DFPase to such signal peptides is advantageous in order to prevent the formation of inclusion bodies, that is to say DFPase aggregates within the cell, and to pass larger amounts of protein into the periplasmic space or the medium.

mation of prokaryotic cells with exogenous nucleic acid sequences is familiar to the person skilled in the area of molecular biology. The cell according to the invention may, however, also be a eukaryotic cell such as, for example, a fungus cell (for example yeast), an animal or plant cell. Preferred eukaryotic expression systems are, for example, *Pichia pastoris* or *Saccharomyces cerevisiae*. The transformation or transfection of eukaryotic cells with exogenous nucleic acid sequences is familiar to a person skilled in the area of molecular biology and therefore needs no further explanation.

The provision of the abovementioned proteins, DNA sequences, vectors and transformed cells makes the industrial production of an enzyme with DFPase activity possible. This makes it possible for the first time to degrade, in a simple, economic and environmentally compatible manner, large quantities of acetylcholinesterase inhibitors.

This may entail the DFPase being obtained by recombinant DNA technology as a constituent of an extract from the host organism or in isolated and purified form, for example by expression in *E. coli*. The use according to the invention of such a DFPase comprises the degradation of P—F linkages or of acetylcholinesterase inhibitors corresponding to the basic formula and containing P—Y linkages. It is possible and preferred for this purpose to employ the purified and isolated DFPase for example for the industrial cleavage of acetylcholinesterase inhibitors containing P—Y linkages (corresponding to the basic formula) in an enzyme reactor. The immobilization of enzymes in such a reactor is familiar to the skilled person and therefore need not be described in detail here. It is conceivable inter alia to polymerize the DFPase into foams such as, for example, polyurethane foams. Another embodiment of the use is, for example, the use of the DFPase in an intact microorganism which can be employed, for example, for decontaminating soils outdoors, and transformed soil bacteria are preferably employed in this case. A further use according to the invention comprises employing a DFPase according to the invention in a foam, where the foam acts as carrier and/or wetting substance. A foam of this type may be a surfactant foam which can be employed inter alia for decontaminating soils, surfaces, valuable equipment or the like. In some cases, a simple spraying, that is to say application as aerosol, may also suffice. The use in foam form is then not necessarily obligatory. It is also conceivable to use the DFPase in methods operating in a stationary manner and making use, for example, of reactors, and to use the DFPase in a mobile manner for the decontamination of equipment or large areas outdoors. Further embodiments according to the invention of the use of the DFPase may therefore also comprise the detoxification of contaminated watercourses or of drinking water. Immobilization of the enzyme by use thereof as stationary phase in a reactor can take place, for example, by covalent linkage of the enzyme to a solid carrier.

The coding cDNA may have a "His tag" attached, which makes it possible to produce a modified DFPase. This modified DFPase is able to bind to carrier material modified with nickel NTA. If the carrier material modified with nickel NTA is the packing material for a separating column, this method can be used for purifying the DFPase.

It is furthermore possible to impregnate textiles with the enzyme by covalent or noncovalent linkage in order to serve as protective clothing.

One use according to the invention may also consist of novel methods of detection, for example biosensors. In this case, the DFPase acts as receptor which is immobilized on a transducer. If the DFPase cleaves the analyte to be detected, that is to say the substrates described above, the biological signal is transformed into a corresponding measurable electrical signal which is amplified by an electronic component. The final signal is generally related to the quantity and/or nature of the analyte. The DFPase can in this case be present as receptor in pure isolated form or in the cell expressing it. Suitable transducers are the transformer components known to the person skilled in the area of biosensors.

A further use according to the invention is the provision of medicinal products which contain the DFPase as active ingredient and are thus able to contribute to detoxifying or treating a human or animal poisoned with an acetylcholinesterase inhibitor containing P—Y linkages. Suitable for this besides local administration is also parenteral or oral administration.

The present invention further relates to a method for producing a DFPase in which the latter is produced by the cell according to the invention. This method thus contrasts with a complete chemical synthesis of the DFPase. In the method according to the invention for producing a DFPase by a transformed cell, the transformation with an expression vector is preceded by the following steps,
(1) isolation of the mRNA of *Loligo vulgaris* from the head ganglia thereof which have been removed immediately after sacrifice and which should be immediately deep-frozen in liquid nitrogen,
(2) purification of the mRNA by affinity chromatography on an oligo-(dR)-cellulose column,
(3) translation of the mRNA into cDNA.
(4) cloning of the cDNA into λ phages,
(5) finding the λ phages containing the genetic information of the DFPase by means of degenerate probes using the polymerase chain reaction,
(6) amplification of the genetic information by means of the polymerase chain reaction,
(7) transferring the genetic information into an expression vector.

In this method it was necessary to overcome various difficulties which the person skilled in the area of genetic engineering could not have solved with the standard techniques available to him. Thus, for example, it was not obvious, but was absolutely necessary, to isolate the mRNA from *Loligo vulgaris* from the head ganglia of a freshly sacrificed animal, it being necessary to store the head ganglia in liquid nitrogen immediately after their removal. If this procedure is not followed, the chances of isolating a full length mRNA of the DFPase are virtually zero. The small number of DFPase-encoding mRNA molecules moreover makes it absolutely necessary to use the polymerase chain reaction technique. To find the genetic information in the cDNA bank it was furthermore necessary to develop highly specific probes which had to agree in long regions with the cDNA from *Loligo vulgaris*. Synthesis of these probes was furthermore impeded by the fact that, at the time of the invention, no relatively long protein sequences of the DFPase from *Loligo vulgaris* which would have made it possible to synthesize highly specific probes were known. The person skilled in the area of molecular biology is able to synthesize such probes in a simple manner only through the sequence information provided in the present invention.

The following example is intended to illustrate the invention.

EXAMPLE

Isolation of the Head Ganglia from *Loligo vulgaris* and Subsequent Expression of Recombinant Proteins in *Escherichia Coli*

(1) To isolate the head ganglia, the head of the squid is separated from the visceral sac, and the tentacles are removed. The epidermis is then slightly raised in order to make an incision extending from the oral cavity to the back of the head. The head capsule and the eye are exposed. After removal of all nerve tracts, the brain tissue is removed. Immediately after the isolation, the brain tissue is transferred to liquid nitrogen and stored at −196° C. until the RNA is prepared.

All the glass apparatus is dried at 250° C. for 4 hours. All the solutions are treated as far as possible with diethyl pyrocarbonate. The brain tissue is transferred into a mortar filled with liquid nitrogen and ground to a homogeneous paste. The tissue is then transferred into a citrate buffer which contains guanidinium thiocyanate, β-mercaptoethanol and N-lauroylsarcosine. A glass Potter homogenizer is used to break up small cell fragments still present in the cell lysate obtained. Before carrying out the ultracentrifugation, tissue particles still present are removed from the homogenate by centrifugation. An ultracentrifugation with a caesium chloride gradient is then carried out to remove the RNA from other cell constituents. The pellet from the centrifugation is washed with ethanol and, after dissolving in water, extracted several times with phenol/chloroform. The usual tests are carried out to check the quality and quantity of the RNA.

(2) The mRNA is concentrated by an affinity chromatography on oligo-(dT)-cellulose. For this purpose, after preparation of an affinity chromatography column, the complete RNA is heated and then cooled in an ice bath. After breaking up the secondary structures, the complete RNA is loaded onto the oligo-(dT)cellulose column at high salt concentrations. This entails the poly-(A⁺) RNA being specifically bound to the carrier material. In order to increase the yield of mRNA it is advantageous for the eluate to be collected, denatured again and loaded on again. The column with the poly-(A⁺) RNA bound thereon is washed with loading and washing buffers. The poly-(A+) RNA is eluted from the loaded oligo-(dT)-cellulose by a solution of low salt concentration, and the suitable fractions are determined by spectrophotometry.

(3) The first cDNA strand is synthesized using an oligo-(dT) primer which, besides the poly-(dT) sequence necessary for the binding, contains an XhoI cleavage site and a "GAGA" sequence. After formation of the hybrid, a DNA strand complementary to the mRNA is synthesized by reverse transcriptase. The reverse transcriptase used for this reaction is that from Moloney murine leukaemia virus (M-MuL VRT) because of its relatively low RNase H activity, the higher processivity and the smaller possibility of inhibition by poly-(A⁻) RNA. To protect from restriction enzyme digestion in the synthesis, a mixture of dATP, dGTP, dTTP and 5-methyl-dCTP is used for the first strand. After the synthesis, the *Escherichia coli* bacterial strain PKL-F' which carries the genetic markers mcrA⁻ and mcrB⁻ is used for the first rounds of replication.

Following the synthesis of the first cDNA strand, the second strand is synthesized by the method of Gubler and Hoffman. Firstly, the endoribonuclease RNase H is used to cleave the RNA of the RNA:DNA double strand. This results in oligoribonucleotides with 5'-phosphate and 3'-hydroxy ends which are recognized by DNA polymerase I and are used as starters for the DNA synthesis.

In order to be able to clone the resulting DNA double strand into a suitable vector, in a first step protruding ends of the DNA strands are filled in by treatment with T4 DNA polymerase. Then T4 DNA ligase is used to provide EcoRI adapters on the cDNA ends. This entails use of a mixture of a phosphorylated 9mer and of a dephosphorylated 13mer oligodeoxyribonucleotide. After thermal inactivation of the ligase, the protruding 5' ends are phosphorylated by T4 polynucleotide kinase, and the DNA double strand is then cut with the restriction enzyme XhoI. Directed cloning into a suitable vector is possible by using two different restriction cleavage sites at the cDNA ends.

(4) The resulting cDNA is cloned into the vector arms of bacteriophage λ. Viable bacteriophages are obtained by in vitro packaging in previously prepared phage heads and incubation with various cell extracts of phage mutants. Two cDNA banks with different numbers of recombinant vector molecules are constructed and serve as starting points for further studies.

(5) To screen the two cDNA banks for the genetic information of diisopropyl-fluorophosphatase, oliogodeoxyribonucleotides intended to have the greatest possible agreement with the cDNA sequence of the protein are designed using the previously elucidated partial information about the amino acid sequence of the protein—with the assistance of other techniques. It is possible to generate products by using the polymerase chain reaction with a sequence-specific oliogodeoxyribonucleotide—of the sequence 5'-TTC-CAA-TTC-CCI-AAT-GGI-ATT-GCT-GT-3' (SEQ ID NO: 3)—under very stringent conditions. Two oligodeoxyribonucleotides are used in the PCR experiments to identify the diisopropyl-fluorophosphatase from *Loligo vulgaris*. The first oligodeoxyribonucleotide consists of a sequence of bacteriophage λ which is connected to the cDNA sequence cloned in. The second oligodeoxyribonucleotide, which contains inosine in some positions, is derived from the elucidated protein sequence and is therefore specific for the diisopropyl-fluorophosphatase from *Loligo vulgaris*.

Starting from this partial sequence of the enzyme it is possible to elucidate the complete cDNA sequence of the diisopropyl-fluorophosphatase with a total length of 1210 bp. This DNA sequence is characterized by a region about 210 bp long and containing no coding DNA sequence at the 5' end. The open reading frame consists of 942 bp and codes for a protein with 314 amino acids, which has a molecular weight of about 35 kDa.

(6) To set up an expression system, the open reading frame of the enzyme is amplified in a polymerase chain reaction using flanking oligodeoxyribonucleotides. In addition to the protein sequence-specific information, the oligodeoxyribonucleotides contain restriction cleavage sites which simplify cloning into an expression system. An Nco I cleavage site is introduced on the 5' side of the information, and a Hind III cleavage site is inserted on the 3' side of the DNA. The product of the polymerase chain reaction is "blunted" using Pfu Taq polymerase, purified on an agarose gel, isolated and transformed into the opened vector pCR-Script SK(+).

(7) After selection of the plasmids which contain the genetic information which is sought, the latter is cut out with Nco I/Hind III and transformed into an expression vector with trc promoter system. It is possible by expression in this system to obtain 150–200 mg of recombinant and biologically active diisopropyl-fluorophosphatase per litre of medium.

What is claimed is:

1. An isolated recombinant protein comprising an amino acid sequence set forth in SEQ ID NO: 1 and being capable of hydrolyzing organophosphorous acetylcholinesterase inhibitors.

2. The isolated recombinant protein of claim 1 consisting of an amino acid sequence set forth in SEQ ID NO: 1.

3. The isolated recombinant protein of claim 1 comprising an amino acid sequence set forth in SEQ ID NO: 1 and being capable of hydrolyzing organophosphorous acetylcholinesterase inhibitors having the structure:

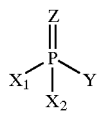

where Z represents oxygen or sulphur; Y represents an anhydride group, fluoro, a CN group or an ester group; and $X_1$ and $X_2$ each represent a straight-chain, branched or cyclic alkoxy, alkyl, aryl, alkylamino or dialkylamino group containing 1 to 15 carbon atoms, where $X_1$ and $X_2$ are identical or different.

4. An isolated recombinant protein comprising an amino acid sequence set forth in SEQ ID NO: 1 and having a DFPase activity.

5. An isolated nucleic acid sequence comprising a nucleic acid sequence which codes for a polypeptide having a DFPase activity, wherein the polypeptide comprises the amino acid sequence set forth in SEQ ID NO: 1.

6. A vector comprising at least one copy of the nucleic acid sequence of claim 5.

7. A cell transformed with the vector of claim 6.

8. A cell transformed with the nucleic acid sequence of claim 5.

9. The transformed cell of claim 8, which is a transformed *E. coli* cell.

10. The transformed cell of claim 8, which is a soil bacterium.

11. The nucleic acid sequence of claim 5 comprising a nucleic acid sequence set forth in SEQ ID NO: 2.

12. A cell transformed with the nucleic acid sequence of claim 11.

13. The transformed cell of claim 8, which is an eukaryotic cell.

14. An isolated nucleic acid sequence comprising a nucleic acid sequence which codes for a polypeptide being capable of hydrolyzing organophosphorous acetylcholinesterase inhibitors, wherein the polypeptide comprises SEQ ID NO: 3.

15. The isolated nucleic acid sequence of claim 14 comprising a nucleic acid sequence which codes for a polypeptide being capable of hydrolyzing organophosphorous acetylcholinesterase inhibitors having the structure:

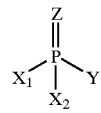

where Z represents oxygen or sulphur; Y represents an anhydride group, fluoro, a CN group or an ester group; and $X_1$ and $X_2$ each represent a straight-chain, branched or cyclic alkoxy, alkyl, aryl, alkylamino or dialkylamino group containing 1 to 15 carbon atoms, where $X_1$ and $X_2$ are identical or different, wherein the polypeptide comprises SEQ ID NO: 1.

16. A method for production of a diisopropylfluorophosphatase comprising transforming or transfecting a cell with the nucleic acid sequence of claim 5; and expressing said transformed or transfected nucleic acid sequence.

17. A method for degradation of an acetylcholinesterase inhibitor comprising degrading the acetylcholinesterase inhibitor with the protein of claim 1; wherein the acetylcholinesterase inhibitor includes a P—Y linkage and has a structure:

$$\underset{X_2}{\overset{\overset{Z}{\|}}{X_1\diagup P\diagdown Y}}$$

where Z represents oxygen or sulphur; Y represents an anhydride group, fluoro, a CN group or an ester group; and $X_1$ and $X_2$ each represent a straight-chain, branched or cyclic alkoxy, alkyl, aryl, alkylamino or dialkylamino group containing 1 to 15 carbon atoms, where $X_1$ and $X_2$ are identical or different.

18. The method of claim 17 wherein Y represents a thioester group, an enol ester group or a p-nitrophenyl ester group.

19. The method of claim 17 wherein Y represents fluoro or a CN group.

20. The method of claim 17 wherein the protein is immobilized in an enzyme reactor.

21. The method of claim 17 comprising degrading the acetylcholinesterase inhibitor in drinking water or a watercourse with the protein.

22. The method of claim 17 wherein the protein is immobilized on or in a carrier material.

23. The method of claim 22 wherein the carrier is a textile material.

24. The method of claim 17 wherein the protein is present in an enzyme reactor.

25. The method of claim 17 wherein the protein is employed in the form of an aerosol-forming spray liquid.

26. The method of claim 17 wherein the protein is employed in a surfactant foam.

27. The method of claim 17 comprising degrading the acetylcholinesterase inhibitor in soil or on equipment with the protein.

28. The method of claim 27 wherein the protein is employed in a surfactant foam or in the form of an aerosol-forming spray liquid.

29. A method for preparing a medicinal product to counter poisoning by an acetylcholinesterase inhibitor comprising adding the protein of claim 1 to a carrier to provide the medicinal product.

30. The method of claim 29 wherein the medicinal product is suitable for local, parenteral or oral administration.

31. The method of claim 29 wherein the acetylcholinesterase inhibitor includes a P—Y linkage and has a structure:

$$\underset{X_2}{\overset{\overset{Z}{\|}}{X_1\diagup P\diagdown Y}}$$

where Z represents oxygen or sulphur; Y represents an anhydride group, fluoro, a CN group or an ester group: and $X_1$ and $X_2$ each represent a straight-chain, branched or cyclic alkoxy, alkyl, aryl, alkylamino or dialkylamino group containing 1 to 15 carbon atoms, where $X_1$ and $X_2$ are identical or different.

* * * * *

UNITED STATES PATENT AND TRADEMARK OFFICE
CERTIFICATE OF CORRECTION

PATENT NO.    : 6,524,834 B1
DATED         : February 25, 2003
INVENTOR(S)   : Heinz Ruterjans and Stefan Dierl It is certified that error appears in the above-identified patent and that said Letters Patent is hereby corrected as shown below:

<u>Column 14,</u>
Line 58, following "SEQ ID NO:" delete "3" and substitute -- 1 --.

Signed and Sealed this

Twelfth Day of August, 2003

JAMES E. ROGAN
*Director of the United States Patent and Trademark Office*

SEQUENCE LISTING

<160> NUMBER OF SEQ ID NOS: 3

<210> SEQ ID NO 1
<211> LENGTH: 314
<212> TYPE: PRT
<213> ORGANISM: Loligo vulgaris

<400> SEQUENCE: 1

Met Glu Ile Pro Val Ile Glu Pro Leu Phe Thr Lys Val Thr Glu Asp
 1               5                  10                  15

Ile Pro Gly Ala Glu Gly Pro Val Phe Asp Lys Asn Gly Asp Phe Tyr
            20                  25                  30

```
Ile Val Ala Pro Glu Val Glu Val Asn Gly Lys Pro Ala Gly Glu Ile
         35                  40                  45
Leu Arg Ile Asp Leu Lys Thr Gly Lys Lys Thr Val Ile Cys Lys Pro
 50                  55                  60
Glu Val Asn Gly Tyr Gly Gly Ile Pro Ala Gly Cys Gln Cys Asp Arg
 65                  70                  75                  80
Asp Ala Asn Gln Leu Phe Val Ala Asp Met Arg Leu Gly Leu Leu Val
                 85                  90                  95
Val Gln Thr Asp Gly Thr Phe Glu Ile Ala Lys Lys Asp Ser Glu
                100                 105                 110
Gly Arg Arg Met Gln Gly Cys Asn Asp Cys Ala Phe Asp Tyr Glu Gly
            115                 120                 125
Asn Leu Trp Ile Thr Ala Pro Ala Gly Glu Val Ala Pro Ala Asp Tyr
        130                 135                 140
Thr Arg Ser Met Gln Glu Lys Phe Gly Ser Ile Tyr Cys Phe Thr Thr
145                 150                 155                 160
Asp Gly Gln Met Ile Gln Val Asp Thr Ala Phe Gln Phe Pro Asn Gly
                165                 170                 175
Ile Ala Val Arg His Met Asn Asp Gly Arg Pro Tyr Gln Leu Ile Val
            180                 185                 190
Ala Glu Thr Pro Thr Lys Lys Leu Trp Ser Tyr Asp Ile Lys Gly Pro
        195                 200                 205
Ala Lys Ile Glu Asn Lys Lys Val Trp Gly His Ile Pro Gly Thr His
    210                 215                 220
Glu Gly Gly Ala Asp Gly Met Asp Phe Asp Glu Asp Asn Asn Leu Leu
225                 230                 235                 240
Val Ala Asn Trp Gly Ser Ser His Ile Glu Val Phe Gly Pro Asp Gly
                245                 250                 255
Gly Gln Pro Lys Met Arg Ile Arg Cys Pro Phe Glu Lys Pro Ser Asn
            260                 265                 270
Leu His Phe Lys Pro Gln Thr Lys Thr Ile Phe Val Thr Glu His Glu
        275                 280                 285
Asn Asn Ala Val Trp Lys Phe Glu Trp Gln Arg Asn Gly Lys Lys Gln
    290                 295                 300
Tyr Cys Glu Thr Leu Lys Phe Gly Ile Phe
305                 310

<210> SEQ ID NO 2
<211> LENGTH: 942
<212> TYPE: DNA
<213> ORGANISM: Loligo vulgaris

<400> SEQUENCE: 2
atggaaattc cagttatcga acctcttttc acaaaagtga ccgaagatat accaggtgca      60
gagggtcccg ttttgacaa aaatggcgat ttttatatcg tggcccccga agttgaagtt     120
aacggaaaac cggcgggaga aattctacga atcgatttga aaacaggaaa gaaaactgtg     180
atctgcaaac cagaagttaa tggttatgga ggaattcctg ctggctgcca atgtgatcga     240
gatgccaacc agctgtttgt ggccgacatg agactcggct tgttggtcgt gcaaactgat     300
gggacctttg aagagattgc caaaaaagac tctgaaggta agaatgca gggatgcaat     360 gattgcgcat ttgattatga aggtaacttg tggatcactg caccagctgg ggaagtcgca     420
cctgcagact acacccgttc aatgcaggaa aaatttggca gtatttactg cttcacaaca     480
gatggtcaaa tgattcaagt ggatactgct ttccagtttc caaatggtat tgctgttcgt     540
```

```
cacatgaacg atggccgtcc ttaccaacta attgtggctg aaactccaac caagaaactc        600
tggagttatg atatcaaagg tccagcaaag attgaaaaca agaaagtgtg gggtcacatc        660
ccaggtactc atgaaggtgg tgctgatgga atggattttg atgaagacaa taaccttttg        720
gtagccaact gggggagctc acacatcgaa gtgttcggcc cagatggggg acagcctaaa        780
atgagaatcc gttgcccatt tgaaaaaccc agcaacttgc atttcaagcc ccagaccaaa        840
accatttttg tcacggaaca cgagaacaat gctgtctgga agtttgaatg gcaaagaaat        900
ggcaaaaaac agtattgtga gacgttaaaa tttggaatat tt                          942
```

```
<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide
<221> NAME/KEY: modified_base
<222> LOCATION: (1)..(26)
<223> OTHER INFORMATION: "n" represents an inosine

<400> SEQUENCE: 3
ttccaattcc cnaatggnat tgctgt                                              26
```